US012773486B2

(12) United States Patent
Lupton et al.

(10) Patent No.: US 12,773,486 B2
(45) Date of Patent: Oct. 27, 2026

(54) PROCESS FOR REMOVING IONS FROM BODILY FLUIDS USING SMALL MOLECULE METAL CHELATORS AND METALLATE ION EXCHANGE COMPOSITIONS

(71) Applicant: UOP LLC, Des Plaines, IL (US)

(72) Inventors: Francis Stephen Lupton, Evanston, IL (US); Gregory J. Lewis, Santa Cruz, CA (US); James M. Hodges, Evanston, IL (US); Paulina Jakubczak, Elk Grove Village, IL (US); Mimoza Sylejmani-Rekaliu, Bensenville, IL (US); William Sheets, Glenview, IL (US)

(73) Assignee: UOP LLC, Rosemont, IL (US)

( * ) Notice: Subject to any disclaimer, the term of this patent is extended or adjusted under 35 U.S.C. 154(b) by 1410 days.

(21) Appl. No.: 17/396,035

(22) Filed: Aug. 6, 2021

(65) Prior Publication Data

US 2022/0096724 A1 Mar. 31, 2022

Related U.S. Application Data

(60) Provisional application No. 63/085,834, filed on Sep. 30, 2020.

(51) Int. Cl.

| | |
|---|---|
| *A61M 1/36* | (2006.01) |
| *A61K 31/10* | (2006.01) |
| *A61K 31/194* | (2006.01) |
| *A61K 31/198* | (2006.01) |
| *A61K 31/341* | (2006.01) |
| *A61K 31/35* | (2006.01) |
| *A61K 31/4184* | (2006.01) |
| *A61K 31/44* | (2006.01) |
| *A61K 33/24* | (2019.01) |
| *A61K 38/06* | (2006.01) |
| *A61M 1/28* | (2006.01) |
| *B01D 15/36* | (2006.01) |
| *B01D 69/08* | (2006.01) |
| *B01D 69/14* | (2006.01) |

(52) U.S. Cl.

CPC ........... *A61M 1/3687* (2013.01); *A61K 31/10* (2013.01); *A61K 31/194* (2013.01); *A61K 31/198* (2013.01); *A61K 31/341* (2013.01); *A61K 31/35* (2013.01); *A61K 31/4184* (2013.01); *A61K 31/44* (2013.01); *A61K 33/24* (2013.01); *A61K 38/063* (2013.01); *A61M 1/28* (2013.01); *B01D 15/361* (2013.01); *B01D 69/08* (2013.01); *B01D 69/147* (2013.01)

(58) Field of Classification Search

None

See application file for complete search history.

(56) References Cited

U.S. PATENT DOCUMENTS

| | | | |
|---|---|---|---|
| 4,261,828 | A | 4/1981 | Brunner et al. |
| 4,581,141 | A | 4/1986 | Ash |
| 4,612,122 | A | 9/1986 | Ambrus et al. |
| 5,519,058 | A | 5/1996 | Gonick et al. |
| 5,536,412 | A | 7/1996 | Ash |
| 5,888,472 | A | 3/1999 | Bem et al. |
| 5,891,417 | A | 4/1999 | Bem et al. |
| 6,099,737 | A | 8/2000 | Sherman et al. |
| 6,332,985 | B1 | 12/2001 | Sherman et al. |
| 6,579,460 | B1 | 6/2003 | Willis et al. |
| 6,814,871 | B1 | 11/2004 | Bem et al. |
| 8,802,152 | B2 | 8/2014 | Keyser et al. |
| 8,808,750 | B2 | 8/2014 | Keyser et al. |
| 8,877,255 | B2 | 11/2014 | Keyser et al. |
| 9,033,908 | B2 | 5/2015 | Schilthuizen et al. |
| 9,457,050 | B2 | 10/2016 | Keyser et al. |
| 9,662,352 | B2 | 5/2017 | Keyser et al. |
| 9,707,255 | B2 | 7/2017 | Keyser et al. |
| 9,844,567 | B2 | 12/2017 | Keyser et al. |
| 9,861,658 | B2 | 1/2018 | Keyser et al. |
| 9,943,637 | B2 | 4/2018 | Keyser et al. |
| 10,398,730 | B2 | 9/2019 | Keyser et al. |
| 10,413,569 | B2 | 9/2019 | Keyser et al. |

(Continued)

FOREIGN PATENT DOCUMENTS

| | | | |
|---|---|---|---|
| EP | 0046971 | A1 | 3/1982 |
| GB | 1132233 | A | 10/1968 |
| WO | 0066198 | A1 | 11/2000 |

OTHER PUBLICATIONS

Office Action for corresponding Brazil Application No. BR1120230057272 dated Sep. 4, 2024.

Search Report for corresponding EP Application No. 21926038.7.

Flora et al: "Chelation in Metal Intoxication", Ineternation Journal of Environmental Research and Public Health, vol. 7, No. 12. Jun. 28, 2010 (Jun. 28, 2010).

Tandon et al: "Mobilization of lead by calcium versenate and Dimercaptosuccinate in the rat", Clinical and experimental pharmacology and physiology, Wiley Blackwell publishing Asia, Au, vol. 25, No. 9, Jun. 28, 2007 (Jun. 28, 2007).

Sinider T H et al : "Arsenic distribution in rabbits after Lewisite administration and treatment with British anti-Lewisite (BAL)", Fundamental and Applied Toxicolofy, Society of Toxicology, Akron, OH, US, vol. 14, No. 2, Feb. 1, 1990 (Feb. 1, 1990).

(Continued)

*Primary Examiner* — Robert A Wax
*Assistant Examiner* — Quanlong N Truong
(74) *Attorney, Agent, or Firm* — Paschall & Associates, LLC; Mark Goldberg

(57) ABSTRACT

A process for removing $Pb^{2+}$, $Hg^{2+}$ and other heavy metal toxins from bodily fluids is disclosed. The process involves treating a patient with a small molecule heavy metal chelator to remove these toxins from bones and soft tissue cells into the blood or other bodily fluid. Then an ion exchange composition is used to ion exchange the heavy metal toxins from bodily fluids either within the body or by treatment outside the body such as by dialysis. The ion exchange compositions may be supported by porous networks of biocompatible polymers such as carbohydrates or proteins.

9 Claims, No Drawings

(56) References Cited

U.S. PATENT DOCUMENTS

| | | | | |
|---|---|---|---|---|
| 10,695,365 | B2 | 6/2020 | Keyser et al. | |
| 2005/0106267 | A1* | 5/2005 | Frykman | A61K 33/06 424/684 |
| 2009/0011048 | A1* | 1/2009 | Coleman | A23L 33/15 424/641 |
| 2014/0056976 | A1 | 2/2014 | Pronovost et al. | |
| 2016/0038538 | A1 | 2/2016 | Keyser et al. | |
| 2018/0369279 | A1 | 12/2018 | Frykman et al. | |

OTHER PUBLICATIONS

Kalodynska D et al: "Chromium and Arsenic Removal in the Presence of Complexing Agent of New Generation", Wastewater treatment, Jan. 1, 2020 (Jan. 1, 2020).

Alicia P. Schroder et al., Lead Toxicity and Chelation Therapy, U.S. Pharmacist, May 15, 2015, 1-12.

Stuart E. Lind et al., Pyrithione and 8-hydroxyquinolines transport lead across erthrocyte membranes, Department of Medicine, University of Colorado, Jun. 10, 2009, 153-159.

* cited by examiner

PROCESS FOR REMOVING IONS FROM BODILY FLUIDS USING SMALL MOLECULE METAL CHELATORS AND METALLATE ION EXCHANGE COMPOSITIONS

CROSS REFERENCE

This application claims priority to provisional application 63/085834, filed Sep. 30, 2020.

FIELD OF THE INVENTION

This invention relates to extracorporeal or intracorporeal processes for removing lead and other ions from bodily fluids. The blood or other bodily fluid is contacted directly with a metallate ion exchange composition and a small molecule metal chelator which are capable of selectively removing the toxins. The small molecule metal chelators are effective in removing the ions from the cell so that the metallate ion exchange composition can then absorb lead and other metal ions.

BACKGROUND OF THE INVENTION

In mammals, e.g., humans, when the kidneys and/or liver fail to remove metabolic waste products from the body, most of the other organs of the body also soon fail. Accordingly, extensive efforts have been made to discover safe and effective methods for removing toxins from patients' blood by extracorporeal treatment of the blood. Many methods have been proposed for removing small molecular toxins, protein-bound molecules or larger molecules thought to be responsible for the coma and illness of hepatic failure. Some of these toxic compounds have been identified as urea, creatine, ammonia, phenols, mercaptans, short chain fatty acids, aromatic amino acids, false neural transmitters (octopamine), neural inhibitors (glutamate) and bile salts. The art shows a number of ways to treat blood containing such toxins. The classic method is of course, dialysis. Dialysis is defined as the removal of substances from a liquid by diffusion across a semipermeable membrane into a second liquid. Dialysis of blood outside of the body (hemodialysis) is the basis of the "artificial kidney." The artificial kidney treatment procedure generally used today is similar to that developed by Kolff in the early 1940s. Since the 1940s there have been several disclosures which deal with improvements on artificial kidneys or artificial livers. Thus, U.S. Pat. No. 4,261,828 discloses an apparatus for the detoxification of blood. The apparatus comprises a housing filled with an adsorbent such as charcoal or a resin and optionally an enzyme carrier. In order to prevent direct contact between the blood and the adsorbent, the adsorbent may be coated with a coating which is permeable for the substances to be adsorbed yet prevent the direct contact between the corpuscular blood components and the adsorbents. U.S. Pat. No. 4,581,141 discloses a composition for use in dialysis which contains a surface adsorptive substance, water, a suspending agent, urease, a calcium-loaded cation exchanger, an aliphatic carboxylic acid resin and a metabolizable organic acid buffer. The calcium loaded cation exchanger can be a calcium-exchanged zeolite. EP 0046971 A1 discloses that zeolite W can be used in hemodialysis to remove ammonia. Finally, U.S. Pat. No. 5,536,412 discloses hemofiltration and plasma filtration devices in which blood flows through the interior of a hollow fiber membrane and during the flow of blood, a sorbent suspension is circulated against the exterior surfaces of the hollow fiber membrane. Another step involves having the plasma fraction of the blood alternately exit and re-enter the interior of the membrane thereby effectuating removal of toxins. The sorbent can be activated charcoal along with an ion-exchanger such as a zeolite or a cation-exchange resin.

There are problems associated with the adsorbents disclosed in the above patents. For example, charcoal does not remove any water, phosphate, sodium or other ions. Zeolites have the disadvantage that they can partially dissolve in the dialysis solution, allowing aluminum and/or silicon to enter the blood. Additionally, zeolites can adsorb sodium, calcium and potassium ions from the blood thereby requiring that these ions be added back into the blood.

More recently, examples of microporous ion exchangers that are essentially insoluble in fluids, such as bodily fluids (especially blood), have been developed, namely the zirconium-based silicates and titanium-based silicates of U.S. Pat. Nos. 5,888,472; 5,891,417 and U.S. Pat. No. 6,579,460. The use of these zirconium-based silicate or titanium-based silicate microporous ion exchangers to remove toxic ammonium cations from blood or dialysate is described in U.S. Pat. Nos. 6,814,871, 6,099,737, and U.S. Pat. No. 6,332,985. Additionally, it was found that some of these compositions were also selective in potassium ion exchange and could remove potassium ions from bodily fluids to treat the disease hyperkalemia, which is discussed in patents U.S. Pat. Nos. 8,802,152; 8,808,750; 8,877,255; 9,457,050; U.S. Pat. No. 9,662,352; U.S. Pat. No. 9,707,255; U.S. Pat. No. 9,844,567; 9,861,658; 10,413,569; 10,398,730; US2016/0038538 and U.S. Pat. No. 10,695,365. Ex-vivo applications of these materials, for instance in dialysis, are described in U.S. Pat. No. 9,943,637.

Blood compatible polymers have also been incorporated into devices for treating bodily fluids. U.S. Pat. No. 9,033,908 discloses small desktop and wearable devices for removing toxins from blood. The device features a sorption filter that utilizes nanoparticles embedded in a porous blood compatible polymeric matrix. Among the toxic materials targeted by this device and filter system are potassium, ammonia, phosphate, urea, and uric acid. Similarly, a 3-D printed hydrogel matrix consisting of crosslinked poly(ethylene glycol) diacrylate to which poly diacetylene-based nanoparticles are tethered proved successful for removing the toxin melittin (*Nat. Commun.,* 5, 3774, 2014).

Besides toxins derived from metabolic wastes, humans are susceptible to environmental toxins that may enter the body, for instance, by ingestion, absorption through the skin or inhalation. A common well-known toxic metal is lead. For many years, lead was a key component of gasoline in the form of tetraethyl lead and a key component of paints. Currently lead is no longer used or rarely used in these industries, but there are still environmental dangers. Remodeling activities on old homes painted with lead-containing paints produce dusts that may be inhaled or end up in nearby soils, where lead is leached away in ground water or taken up by plants. Unreliable or unregulated water supplies represent a dangerous exposure to $Pb^{2+}$ toxicity, most notably the recent case in Flint, Michigan, USA, in which some residents were found to have dangerously high $Pb^{2+}$ levels in their blood after exposure to a new city water supply source. Lead contamination is associated with many ill health effects, including affecting the nervous and urinary systems and inducing learning and developmental disabilities in exposed children. Removal of lead from the blood of afflicted patients would reduce further exposure and damage.

Another well-known toxic metal is mercury. Most human-generated mercury found in the environment comes from the combustion of fossil fuels, the primary source being coal-burning power plants, although various industrial processes also release mercury into the environment. Environmental mercury bioaccumulates in fish and shellfish in the form of methylmercury, which is a highly toxic form of the heavy metal, and consumption of contaminated seafood is the most common cause of mercury poisoning in humans. Once in the body, methyl mercury is likely converted into divalent mercury, where it feeds into a reduction-oxidation pathway. Another common source of exposure is from dental fillings that are composed of mercury amalgams. Elevated blood levels of mercury can cause a wide variety of illnesses including neurological disturbances and renal failure, and these adverse effects are amplified in children.

Chelation therapy has been used to try to remove some of these metal toxins from blood. Chelation therapy has been directed toward removal $Co^{2+}$, $Cr^{2\times}$ and $Cd^{2+}$ from the blood (J Med Toxicol., (2013) 9, 355-369). Chelation therapy has also been used for $Pb^{2+}$ poisoning, including the chelating agent $CaNa_2EDTA$, which is administered intravenously. (Int. J. Environ. Res. Public Health, (2010), 7, 2745-2788). Dimercaptosuccinic acid (DMSA) was recognized as an antidote for heavy metal poisoning and has been used to treat $Co^{2+}$, $Cd^{2+}$ and $Pb^{2+}$ poisoning (See U.S. Pat. No. 5,519, 058). Supported chelating agents, i.e., chelating agents bound to resins have been used for heavy metal removal in a dialysis mode, where the blood is on one side of a semi-permeable membrane and the resin-supported chelates on the other side (See U.S. Pat. No. 4,612,122). Since chelation therapy is effective to some extent, it would be desirable if it can be made more effective.

Zeolites have been proposed for treating chronic lead poisoning, taken in pill form in U.S. 20180369279A1, but zeolites have limited stability, especially in the gastrointestinal tract.

Applicants have developed a process which uses a treatment combining the use of ionophores or chelating agents in combination with metallate ion exchangers which are essentially insoluble in fluids, such as bodily fluids (especially blood) or dialysis solutions.

SUMMARY OF THE INVENTION

As stated, this invention relates to a process for removing $Pb^{2+}$, $Hg^{2+}$, and other metal ions from fluids selected from the group consisting of a bodily fluid, a dialysate solution and mixtures thereof. The process comprises contacting the fluid containing the toxins with an ionophore or a chelating agent which is especially useful in transporting the ions across a cell membrane. At the same time or subsequently is used to an ion exchanged microporous composition, also referred to as a metallate ion exchanger, thereby removing the toxins from the fluid. The chelating agents may be selected from 2,3-dimercaptopropanol, 2,3-dimercaptosuccinic acid, ethylenediaminetetraacetic acid, glutathione, and cysteine. The ionophores may be selected from monensin, pyrithione, nigericin, ionomycin and A23187. The small molecule heavy metal chelators and ionophores act to form a complex with metal ions such as $Pb^{2+}$ and $Hg^{2+}$. In particular, they act to remove these ions from bones and soft tissue and then convey them to the blood and the liver where it is easier to remove the ions. The chelating agents and ionophores that have complexed with the ions may then enter the intestines via bile from the liver or pass by diffusion across the intestine linings where they will encounter the metallate ion exchangers and then the ions are adsorbed into the metallate ion exchangers which then may be excreted from the body through natural body functions. The use of both the chelating agents or ionophores in combination with the metallate ion exchangers can prove to have a synergistic interaction in the removal of lead and other ions from the body.

There are several different ion exchangers that may be used, especially any ion exchangers that previously have shown effectiveness in removing metal ions from the body. One class of ion exchanger, rare earth silicate ion exchangers, is identified by their empirical formulas on an anhydrous basis of:

$$A^{r+}_{p}M^{s+}_{l-x}M'^{t+}_{x}Si_{n}O_{m}$$

In this formula "A" is a structure-directing cation that also serves as a counterbalancing cation and is selected from the group consisting of alkali metals, alkaline earth metals, hydronium ion, ammonium ion, quaternary ammonium ion, and mixtures thereof. Specific examples of alkali metals include, but are not limited to, sodium, potassium and mixtures thereof. Examples of alkaline earth metals include, but are not limited to, magnesium and calcium. "r" is the weighted average valence of A and varies from 1 to 2. The value of "p", which is the mole ratio of "A" to total metal (total metal=M+M') varies from about 1 to about 5. The framework structure is composed of silicon, at least one rare-earth element (M) and optionally an M' metal. The total metal is defined as M+M', where the mole fraction of total metal that is rare earth metals M is given by "l-x" while the mole fraction of total metal that is M' metals is given by "x." The rare-earth elements that are represented by M have a valence of +3 or +4, and include scandium, yttrium, lanthanum, cerium, praseodymium, neodymium, promethium, samarium, europium, gadolinium, terbium, dysprosium, holmium, erbium, thulium, ytterbium, and lutetium. In accordance with these options for M, "s", the weighted average valence of M, varies from 3 to 4. Similarly, more than one M' metal can be present and each M' metal can have a different valence. The M' metals that can be substituted into the framework have a valence of +2, +3, +4, or +5. Examples of these metals include, but are not limited to, zinc (+2), iron (+3), titanium (+4), zirconium (+4), and niobium (+5). Hence, "t", the weighted average valence of M' varies from 2 to 5. Lastly, "n" is the mole ratio of Si to total metal and has a value of about 3 to 10, and "m" is the ratio of O to total metal and is 6ven by $$m = \frac{[(r \cdot p) + (s \cdot (1 - x)) + (t \cdot x) + (4 \cdot n)]}{2}$$

Since the compositions are essentially insoluble in bodily fluids (at neutral and mildly acidic or basic pH), they can be orally ingested to remove heavy metal and metabolic toxins from the gastrointestinal system as well as used to remove toxins from dialysis solutions, especially $Pb^{2+}$, $Hg^{2+}$, $K^+$ and $NH_4^+$.

Another ion exchanger that can be used has an empirical formula on an anhydrous basis of:

$$A_mTi_aNb_{1-a}Si_xO_y$$

where A is an exchangeable cation selected from the group consisting of potassium ion, sodium ion, lithium ion, rubidium ion, cesium ion, calcium ion, magnesium ion, hydronium ion or mixtures thereof, "m" is the mole ratio of A to total metal (total metal=Ti+Nb) and has a value from 0.10 to 2.00, "a" is the mole fraction of total metal that is Ti and has a value from 0.25 to 1, "1−a" is the mole fraction of total metal that is Nb and has a value from zero to 0.75 where a+(1−a)=1, "x" is the mole ratio of Si to total metal and has a value from about 0.25 to 1.50, and "y" is the mole ratio of O to total metal and has a value from 2.55 to about 7.38 and is characterized in that it has the pharmacosiderite topology, sitinakite topology, intergrowths of these two topologies, or mixtures thereof exhibiting an x-ray diffraction pattern having at least one peak with a d-spacing between 7 Å and 8 Å with a relative intensity of 100%, where said diffraction pattern has at least the peaks and d-spacings set forth in Table A when the material has the pharmacosiderite topology:

TABLE A

| 2Θ | d(Å) | $I/I_0\%$ |
|---|---|---|
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m |

or where said diffraction pattern has at least the d-spacings and intensities set forth in Table B when the material has the sitinakite topology:

| 2Θ | d(Å) | $I/I_0\%$ |
|---|---|---|
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m |

or where said diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination.

This and other objects and embodiments will become more clear after a detailed description of the invention.

DETAILED DESCRIPTION OF THE INVENTION

As stated, applicants have developed a new process for removing heavy metal toxins such as $Pb^{2+}$ and $Hg^{2+}$ from fluids selected from the human body. Heavy metals can cause serious harm when they are present in the human body. Lead in particular is of concern due to exposure to old paint and from contaminated drinking water. Microporous inorganic adsorbents, such as metallosilicates have the potential to bind lead and prevent its uptake by cellular tissue in the Ileum. However, once lead is already transported inside the cell, the cell wall's phospholipid bilayer acts as a barrier to the interaction between the ingested lead and the metallosilicate which cannot transfer across the lipid bilayer barrier. The phospholipid bilayer consists of two layers of phospholipids with a hydrophobic, or water-hating, interior and a hydrophilic, or water-loving, exterior. The hydrophilic (polar) head group and hydrophobic tails (fatty acid chains) are found in a single phospholipid molecule.

An ionophore is a chemical species that reversibly binds ions. Many ionophores are lipid-soluble entities that transport ions across a cell membrane. These compounds catalyze ion transport across lipid bilayers found in the living cells. Furthermore, ionophores can be highly selective for specific ions. Some of these ionophores have a high selectivity for lead over other cations. Because of the reversibility of metal binding to the ionophores, the transport of ions in and out of the cell is driven by the equilibrium of metal concentration between the inside and outside cellular cytoplasm. Thus, ionophores can lead to equilibration of an ion such as lead between the concentration of ion ingested and the concentration in the cell. A way to upset the equilibrium such as there is a concentration gradient that promotes transport of lead outside the cell should improve the ability of ionophores to remove this metal from the cell cytoplasm.

The small molecule heavy metal chelator may be selected from 2,3-dimercaptopropanol, 2,3-dimercaptosuccinic acid, ethylenediaminetetraacetic acid, glutathione, and cysteine. Dimercaprol, also called 2,3-dimercaptopropanol has been used in the treatment of arsenic, antimony, lead, gold and mercury poisoning. Ethylenediaminetetraacetic acid (EDTA), also known by several other names, is a chemical used for both industrial and medical purposes. A specific salt of EDTA, known as sodium calcium dedtate, is used to bind metal ions in the practice of chelation therapy such as for treating mercury and lead poisoning as well as to remove excess iron from the body. Glutathione (GSH) is an antioxidant in plants, animals, fungi, and some bacteria and archaea. Glutathione is capable of preventing damage to important cellular components caused by reactive oxygen species such as free radicals, peroxides, lipid peroxides, and heavy metals. Cysteine is a semi-essential proteinogeme amino acid with the formula $HO_2CCH(NH_2)CH_2SH$. The thiol side chain in cysteine often participates in enzymatic reactions, as a nucleophile. The thiol is susceptible to oxidation to give the disulfide derivative cystine, which serves an important structural role in many proteins.

The ionophores that are especially useful in the present invention include monensin, pyrithione, nigericin, ionomycin and A23187. Monensin is a polyether antibiotic isolated from Streptomyces cinnamonensis. It is often referred to as sodium monensin and is a naturally occurring polyether ionophore antibiotic. It is widely used in ruminant animal feeds. In 1967, the structure of monensin was first described by Agtarap et al. and was the first polyether antibiotic to have its structure elucidated (See *J. Am. Chem. Soc.,* 1967, 89, 5737-739). The zinc ionophore pyrithione has been found to have effectiveness against certain virus infections and may be effective in the present application. Nigericin is an antibiotic derived from Streptomyces hygroscopicus. The structure and properties of nigericin are similar to the antibiotic monensin. Ionomycin is an ionophore and an antibiotic that binds calcium ions in a ratio 1:1. It is produced by the bacterium Streptomyces conglobatus. It binds also other divalent cations like magnesium and cadmium but binds $Ca^{2+}$ preferably. It has 14 chiral centers. A23187 is a mobile ion-carrier that forms stable complexes with divalent cations. A23187 is aiso known as Calcimycin, Calcium lonophore, Antibiotic A23187 and Calcium Ionophore A23187. It Is produced by fermentation of *Streptomyces chartreusensis.*

In particular, the chelating agents and ionophores act to remove these ions from bones and soft tissue and then convey them to the blood and the liver where it is easier to remove the ions. The chelating agents and ionophores that have complexed with the ions may then enter the intestines through bile from the liver or pass by diffusion across the intestine linings where they will encounter the metallate ion exchangers and then the ions are adsorbed into the metallate ion exchangers. The ion-containing metallate ion exchangers are then excreted from the body through natural body functions. The use of both the chelating agents or ionophores in combination with the metallate ion exchangers can prove to have a synergistic interaction in the removal of lead and other ions from the body.

One essential element of the instant process is an ion exchanger. In general, ion exchangers that can ion exchange heavy metal ions such as $Pb^{2+}$ and $Hg^{2+}$ are useful in the present invention. One ion exchanger is identified by their empirical formulas on an anhydrous basis of:

$$A^{r+}{}_{p}M^{s+}{}_{1-x}M'^{t+}{}_{x}Si_{n}O_{m}$$

In this formula "A" is a structure-directing cation that also serves as a counterbalancing cation and is selected from the group consisting of alkali metals, alkaline earth metals, hydronium ion, ammonium ion, quaternary ammonium ion, and mixtures thereof. Specific examples of alkali metals include, but are not limited to, sodium, potassium and mixtures thereof. Examples of alkaline earth metals include, but are not limited to, magnesium and calcium. "r" is the weighted average valence of A and varies from 1 to 2. The value of "p", which is the mole ratio of "A" to total metal (total metal=M+M') varies from about 1 to about 5. The framework structure is composed of silicon, at least one rare-earth element (M) and optionally an M' metal. The total metal is defined as M+M', where the mole fraction of total metal that is rare earth metals M is given by "1−x" while the mole fraction of total metal that is M' metals is given by "x." The rare-earth elements that are represented by M have a valence of +3 or +4, and include scandium, yttrium, lanthanum, cerium, praseodymium, neodymium, promethium, samarium, europium, gadolinium, terbium, dysprosium, holmium, erbium, thulium, ytterbium, and lutetium. In accordance with these options for M, "s", the weighted average valence of M, varies from 3 to 4. Similarly, more than one M' metal can be present and each M' metal can have a different valence. The M' metals that can be substituted into the framework have a valence of +2, +3, +4, or +5. Examples of these metals include, but are not limited to, zinc (+2), iron (+3), titanium (+4), zirconium (+4), and niobium (+5). Hence, "t", the weighted average valence of M' varies from 2 to 5. Lastly, "n" is the mole ratio of Si to total metal and has a value of about 3 to 10, and "m" is the ratio of O to total metal and is given by $$m = \frac{[(r \cdot p) + (s \cdot (1 - x)) + (t \cdot x) + (4 \cdot n)]}{2}$$

Since the compositions are essentially insoluble in bodily fluids (at neutral and mildly acidic or basic pH), they can be orally ingested to remove heavy metal and metabolic toxins from the gastrointestinal system as well as used to remove toxins from dialysis solutions, especially $Pb^{2+}$, $Hg^{2+}$, $K^{+}$ and $NH_4^{+}$. These ion-exchangers are described in co-pending patent. . . .

Another ion exchanger that can be used has an empirical formula on an anhydrous basis of:

$$A_{m}Ti_{a}Nb_{1-a}Si_{x}O_{y}$$

where A is an exchangeable cation selected from the group consisting of potassium ion, sodium ion, lithium ion, rubidium ion, cesium ion, calcium ion, magnesium ion, hydronium ion or mixtures thereof, "m" is the mole ratio of A to total metal (total metal=Ti+Nb) and has a value from 0.10 to 2.00, "a" is the mole fraction of total metal that is Ti and has a value from 0.25 to 1, "1−a" is the mole fraction of total metal that is Nb and has a value from zero to 0.75 where a+(1−-a)=1, "x" is the mole ratio of Si to total metal and has a value from about 0.25 to 1.50, and "y" is the mole ratio of O to total metal and has a value from 2.55 to about 7.38 and is characterized in that it has the pharmacosiderite topology, sitinakite topology, intergrowths of these two topologies, or mixtures thereof exhibiting an x-ray diffraction pattern having at least one peak with a d-spacing between 7 Å and 8 ∈ with a relative intensity of 100%, where said diffraction pattern has at least the peaks and d-spacings set forth in Table A when the material has the pharmacosiderite topology:

TABLE A

| 2Θ | d(Å) | $I/I_0$% |
|---|---|---|
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m |

or where said diffraction pattern has at least the d-spacings and intensities set forth in Table B when the material has the sitinakite topology:

| 2Θ | d(Å) | $I/I_0$% |
|---|---|---|
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m |

or where said diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination. These ion exchangers are described in co-pending patent applications 63/085784, 63/085804 and 63/085819, all filed on Sep. 30, 2020 and all incorporated herein in their entireties.

It is also within the scope of the invention that these ion exchange compositions can be used in powder form or can be formed into various shapes by means well known in the art. Examples of these various shapes include pills, extrudates, spheres, pellets and irregularly shaped particles. This has previously been demonstrated in U.S. Pat. No. 6,579,460 B1 and U.S. Pat. No. 6,814,871 B1. The ion exchange compositions of this invention may also be supported, ideally in a porous network including insertion into or binding to a blood compatible porous network such as in a sorption filter as disclosed in U.S. Pat. No. 9,033,908 B2. The porous network may consist of natural or synthetic polymers and biopolymers and mesoporous metal oxides and silicates. Natural polymers (biopolymers) that are suitable may comprise a cross-linked carbohydrate or protein, made of oligomeric and polymeric carbohydrates or proteins. The biopolymer is preferably a polysaccharide. Examples of polysaccharides include a-glucans having 1, 3-, 1, 4- and/or 1, 6-linkages. Among these, the "starch family", including amylose, amylopectin and dextrins, is especially preferred, but pullulan, elsinan, reuteran and other a-glucans, are also suitable, although the proportion of 1, 6-linkages is preferably below 70%, more preferably below 60%. Other suitable polysaccharides include ß-1, 4-glucans (cellulose), ß-1, 3-glucans, xyloglucans, glucomannans, galactans and galactomannans (guar and locust bean gum), other gums including heterogeneous gums like xanthan, ghatti, carrageenans, alginates, pectin, ß-2, 1- and ß-2, 6-fructans (inulin and Ievan), etc. A preferred cellulose is carboxymethylcellulose (CMC, e. g. AKUCELL from AKZO Nobel). Carbohydrates which can thus be used are carbohydrates consisting only of C, H and O atoms such as, for instance, glucose, fructose, sucrose, maltose, arabinose, mannose, galactose, lactose and oligomers and polymers of these sugars, cellulose, dextrins such as maltodextrin, agarose, amylose, amylopectin and gums, e. g. guar. Preferably, oligomeric carbohydrates with a degree of polymerization (DP) from DP2 on or polymeric carbohydrates from DP50 on are used. These can be naturally occurring polymers such as starch (amylose, amylopectin), cellulose and gums or derivates hereof which can be formed by phosphorylation or oxidation. The starch may be a cationic or anionic modified starch. Examples of suitable (modified) starches that can be modified are corn-starch, potato-starch, rice-starch, tapioca starch, banana starch, and manioc starch. Other polymers can also be used (e. g. caprolactone). In certain embodiments, the biopolymer is preferably a cationic starch, most preferably an oxidized starch (for instance C6 oxidized with hypochlorite). The oxidation level may be freely chosen to suit the application of the sorbent material. Very suitably, the oxidation level is between 5 and 55%, most preferably between 25 and 35%, still more preferably between 28% and 32%. Most preferably the oxidized starch is crosslinked. A preferred crosslinking agent is di-epoxide. The crosslinking level may be freely chosen to suit the application of the sorbent material. Very suitably, the crosslinking level is between 0.1 and 25%, more preferably between 1 and 5%, and most preferably between 2.5 and 3. 5%. Proteins which can be used include albumin, ovalbumin, casein, myosin, actin, globulin, hemoglobin, myoglobin, gelatin and small peptides. In the case of proteins, proteins obtained from hydrolysates of vegetable or animal material can also be used. Particularly preferred protein polymers are gelatin or a derivative of gelatin.

As stated, these compositions have particular utility in adsorbing various metal or other toxins, including $Pb^{2+}$ and $Hg^{2+}$, or combinations thereof, from fluids selected from bodily fluids, dialysate solutions, and mixtures thereof. As used herein and in the claims, bodily fluids will include but not be limited to blood, blood plasma and gastrointestinal fluids. Also, the compositions are meant to be used to treat bodily fluids of any mammalian body, including but not limited to humans, cows, pigs, sheep, monkeys, gorillas, horses, dogs, etc. The instant process is particularly suited for removing toxins from a human body. There are a number of means for directly or indirectly contacting the fluids with the desired ion exchanger and thus, remove the toxins. One technique is hemoperfusion, which involves packing the above described ion exchange composition into a column through which blood is flowed. One such system is described in U.S. Pat. No. 4,261,828. As stated in the '828 patent, the ion exchange composition is preferably formed into desired shapes such as spheres. Additionally, the ion exchange composition particles can be coated with compounds, such as cellulose derivatives, which are compatible with the blood but nonpermeable for corpuscular blood components. In one specific case, spheres of the desired ion exchange compositions described above can be packed into hollow fibers thereby providing a semipermeable membrane. It should also be pointed out that more than one type of ion-exchange composition can be mixed and used in the process to enhance the efficiency of the process.

Another way of carrying out the process is to prepare a suspension or slurry of the molecular sieve adsorbent by means known in the art such as described is U.S. Pat. No. 5,536,412. The apparatus described in the '412 patent can also be used to carry out the process. The process basically involves passing a fluid, e.g. blood, containing the metal toxins through the interior of a hollow fiber and during said passing, circulating a sorbent suspension against the exterior surfaces of the hollow fiber membrane. At the same time, intermittent pulses of positive pressure are applied to the sorbent solution so that the fluid alternately exits and reenters the interior of the hollow fiber membrane thereby removing toxins from the fluid.

Another type of dialysis is peritoneal dialysis. In peritoneal dialysis, the peritoneal cavity or the abdominal cavity (abdomen) is filled via a catheter inserted into the peritoneal cavity with a dialysate fluid or solution which contacts the peritoneum. Toxins and excess water flow from the blood through the peritoneum, which is a membrane that surrounds the outside of the organs in the abdomen, into the dialysate fluid. The dialysate remains in the body for a time (dwell time) sufficient to remove the toxins. After the required dwell time, the dialysate is removed from the peritoneal cavity through the catheter. There are two types of peritoneal dialysis. In continuous ambulatory peritoneal dialysis (CAPD), dialysis is carried out throughout the day. The process involves maintaining the dialysate solution in the peritoneal cavity and periodically removing the spent dialysate (containing toxins) and refilling the cavity with a fresh dialysate solution. This is carried out several times during the day. The second type is automated peritoneal dialysis or APD. In APD, a dialysate solution is exchanged by a device at night while the patient sleeps. In both types of dialyses, a fresh dialysate solution must be used for each exchange.

The ion exchangers of the present invention can be used to regenerate the dialysate solutions used in peritoneal dialysis, thereby further decreasing the amount of dialysate that is needed to cleanse the blood and/or the amount of time needed to carry out the exchange. This regeneration is carried out by any of the means described above for conventional dialysis. For example, in an indirect contacting process, the dialysate from the peritoneal cavity, i.e. first dialysate which has taken up metal toxins transferred across the peritoneum is now contacted with a membrane and a second dialysate solution and metal toxins are transferred across a membrane, thereby purifying the first dialysate solution, i.e. a purified dialysate solution. The second dialysate solution containing the metal toxins is flowed through at least one adsorption bed containing at least one of the ion exchangers described above, thereby removing the metal toxins and yielding a purified second dialysate solution. It is usually preferred to continuously circulate the second dialysate solution through the adsorbent bed until the toxic metal ions have been removed, i.e., $P^{2+}$ and, $Hg^{2+}$. It is also preferred that the first dialysate solution be circulated through the peritoneal cavity, thereby increasing the toxic metal removal efficiency and decreasing the total dwell time.

A direct contacting process can also be carried out in which the first dialysate solution is introduced into the peritoneal cavity and then flowed through at least one bed containing at least one ion exchanger. As described above, this can be carried out as CAPD or APD. The composition of the dialysate solution can be varied in order to ensure a proper electrolyte balance in the body. This is well known in the art along with various apparatus for carrying out the dialysis.

The ion exchangers, chelating agents and ionophores can also be formed into pills or other shapes which can be ingested orally and pick up toxins in the gastrointestinal fluid as the ion exchanger passes through the intestines and is finally excreted. In order to protect the ion exchangers from the high acid content in the stomach, the shaped articles may be coated with various coatings which will not dissolve in the stomach, but dissolve in the intestines.

As has also been stated, although the instant compositions are synthesized with a variety of exchangeable cations ("A"), it is preferred to exchange the cation with secondary cations (A') which are more compatible with blood or do not adversely affect the blood. For this reason, preferred cations are sodium, calcium, hydronium and magnesium. Preferred compositions are those containing sodium and calcium or sodium, calcium and hydronium ions. The relative amount of sodium and calcium can vary considerably and depends on the composition and the concentration of these ions in the blood.

Specific Embodiments

While the following is described in conjunction with specific embodiments, it will be understood that this description is intended to illustrate and not limit the scope of the preceding description and the appended claims.

A first embodiment of the invention is a process for removing $Pb^{2+}$ and $Hg^{2+}$ toxins or mixtures thereof from an individual who has at least one of the toxins inside their body comprising administering to the individual a quantity of a small molecule heavy metal chelator or ionophore to complex the toxins within cells within bones and soft tissue in the individual to form a complex comprising the small molecule heavy metal chelator or the ionophore and the toxin wherein the complex passes from the cell to a bloodstream or gastric fluid of the individual and then contacting the bloodstream or gastric fluid containing the complex with an ion exchanger to remove the toxins from the fluid by ion exchange between the ion exchanger and the bodily fluid followed by removal of the ion exchanger from the body. An embodiment of the invention is one, any or all of prior embodiments in this paragraph up through the first embodiment in this paragraph wherein the small molecule heavy metal chelator is selected from 2,3-dimercaptopropanol, 2,3-dimercaptosuccinic acid, ethylenediaminetetraacetic acid, glutathione, and cysteine. An embodiment of the invention is one, any or all of prior embodiments in this paragraph up through the first embodiment in this paragraph wherein the ionophore is capable of transporting at least one of the toxins from inside the cells to the bloodstream. An embodiment of the invention is one, any or all of prior embodiments in this paragraph up through the first embodiment in this paragraph wherein the ionophore is selected from monensin, pyrithione, nigercin, ionomycin and Calcimycin. An embodiment of the invention is one, any or all of prior embodiments in this paragraph up through the first embodiment in this paragraph wherein the ionophore is administered to the individual in an amount of about 0.01 to 0.6 mg/kg body weight of the individual. An embodiment of the invention is one, any or all of prior embodiments in this paragraph up through the first embodiment in this paragraph wherein the ionophore is administered to the individual in an amount of about 0.5 to 0.6 mg/kg body weight of the individual. An embodiment of the invention is one, any or all of prior embodiments in this paragraph up through the first embodiment in this paragraph wherein the ion exchanger is a crystalline metallate ion exchanger selected from titanium silicates and niobium-titanium silicates or mixtures thereof, the metallate having an empirical formula on an anhydrous basis of7

$$A_mTi_aNb_{1-a}Si_xO_y$$

where A is an exchangeable cation selected from the group consisting of lithium ion, potassium ion, sodium ion, rubidium ion, cesium ion, calcium ion, magnesium ion, hydronium ion or mixtures thereof, "m" is the mole ratio of A to total metal (total metal=Ti+Nb) and has a value from 0.10 to 2.0, "a" is the mole fraction of total metal that is Ti and has a value from 0.25 to 1, "1−a" is the mole fraction of total metal that is Nb and has a value from zero to 0.75 where a+(1−a)=1, "x" is the mole ratio of Si to total metal and has a value from about 0.25 to 1.50, and "y" is the mole ratio of O to total metal and has a value from 2.55 to about 7.38 and is characterized in that it has the either the pharmacosiderite topology, sitinakite topology, intergrowths of these two topologies, or mixtures thereof exhibiting an x-ray diffraction pattern having at least one peak with a d-spacing between 7 Å and 8 Å with a relative intensity of 100%, where the diffraction pattern has at least the peaks and d-spacings set forth in Table A when the material has the pharmacosiderite topology

TABLE A

| 2Θ | d(Å) | $I/I_0$% |
|---|---|---|
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m |

or where the diffraction pattern has at least the d-spacings and intensities set forth in Table B when the material has the sitinakite topology

TABLE B

| 2Θ | d(Å) | $I/I_0$% |
|---|---|---|
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m |

or where the diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination. An embodiment of the invention is one, any or all of prior embodiments in this paragraph up through the first embodiment in this paragraph wherein the ion exchanger being a rare-earth silicate composition with an empirical formula on an anhydrous basis of $$A^{r+}_pM^{s+}_{1-x}M'^{t+}_xSi_nO_m$$

where A is an exchangeable cation selected from the group consisting of alkali metals, alkaline earth metals, hydronium ion, ammonium ion, quaternary ammonium ion and mixtures thereof, "r" is the weighted average valence of A and varies from 1 to 2, "p" is the mole ratio of A to total metal (total metal=M+M') and varies from about 1 to about 5, "M" is a framework rare earth metal selected from the group consisting of scandium, yttrium, lanthanum, cerium, praseodymium, neodymium, promethium, samarium, europium, gadolinium, terbium, dysprosium, holmium, erbium, thulium, ytterbium, and lutetium and mixtures thereof, "s" is the weighted average valence of M and varies from 3 to 4, "1−x" is the mole fraction of total metal that is M, M' is a framework metal having a valence of +2, +3, +4, or +5, "t" is the weighted average valence of M' and varies from 2 to 5, "x" is the mole fraction of total metal that is M' and varies from 0 to 0.99, "n" is the mole ratio of Si to total metal and has a value of about 3 to about 10, and "m" is the mole ratio of O to total metal and is given by $$m = \frac{[(r \cdot p) + (s \cdot (1 - x)) + (t \cdot x) + (4 \cdot n)]}{2}.$$

An embodiment of the invention is one, any or all of prior embodiments in this paragraph up through the first embodiment in this paragraph wherein the bodily fluid is selected from the group consisting of whole blood, blood plasma, or other component of blood, gastrointestinal fluids and dialysate solution containing blood, blood plasma, other component of blood or gastrointestinal fluids. An embodiment of the invention is one, any or all of prior embodiments in this paragraph up through the first embodiment in this paragraph wherein the ion exchanger is packed into hollow fibers incorporated into a membrane. An embodiment of the invention is one, any or all of prior embodiments in this paragraph up through the first embodiment in this paragraph wherein the ion exchanger is contained on particles coated with a coating comprising a cellulose derivative composition. An embodiment of the invention is one, any or all of prior embodiments in this paragraph up through the first embodiment in this paragraph wherein the process is a hemoperfusion process wherein the bodily fluid is passed through a column containing the ion exchanger. An embodiment of the invention is one, any or all of prior embodiments in this paragraph up through the first embodiment in this paragraph wherein a dialysate solution is introduced into a peritoneal cavity and then is flowed through at least one adsorbent bed containing at least one of the ion exchanger. An embodiment of the invention is one, any or all of prior embodiments in this paragraph up through the first embodiment in this paragraph wherein the ion exchanger is formed into a shaped article to be ingested orally, followed by ion exchange between the ion exchanger and the $Pb^{2+}$ and, $Hg^{2+}$ toxins contained in a gastrointestinal fluid in a mammal's intestines and then by excretion of the ion exchanger containing the toxins. An embodiment of the invention is one, any or all of prior embodiments in this paragraph up through the first embodiment in this paragraph wherein the shaped article is coated with a coating that is not dissolved by conditions within a stomach.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for removing $Pb^{2+}$, $Hg^{2+}$ and other heavy metal toxins or mixtures thereof from an individual who has at least one of said toxins inside their body comprising administering to said individual a quantity of a small molecule heavy metal chelator or ionophore to complex said toxins within cells within bones and soft tissue in said individual to form a complex comprising said small molecule heavy metal chelator or said ionophore and said toxin wherein said complex passes from said cell to a bloodstream or gastric fluid of said individual and then contacting the bloodstream or gastric fluid containing the complex with an ion exchanger to remove the toxins from the fluid by ion exchange between said ion exchanger and said bodily fluid followed by removal of said ion exchanger from the body, wherein the ion exchanger is a crystalline metallate ion exchanger selected from titanium silicates and niobium-titanium silicates or mixtures thereof, the metallate having an empirical formula on an anhydrous basis of:

$$A_mTi_aNb_{1-a}Si_xO_y$$

where A is an exchangeable cation selected from the group consisting of lithium ion, potassium ion, sodium ion, rubidium ion, cesium ion, calcium ion, magnesium ion, hydronium ion or mixtures thereof, "m" is the mole ratio of A to total metal, wherein (total metal equals Ti plus Nb, and has a value from 0.10 to 2.0, "a" is the mole fraction of total metal that is Ti and has a value from 0.25 to 1, "1-a" is the mole fraction of total metal that is Nb and has a value from zero to 0.75 where a + (1-a) =1, "x" is the mole ratio of Si to total metal and has a value from about 0.25 to 1.50, and "y" is the mole ratio of O to total metal and has a value from 2.55 to about 7.38 and is characterized in that it has the either the pharmacosiderite topology, sitinakite topology, intergrowths of these two topologies, or mixtures thereof exhibiting an x-ray diffraction pattern having at least one peak with a d-spacing between 7 Å and 8 Å with a relative intensity of 100%, where said diffraction pattern has at least the peaks and d-spacings set forth in Table A when the material has the pharmacosiderite topology:

TABLE A

| 2Θ | d(Å) | $I/I_0$% |
|---|---|---|
| 11.394-11.163 | 7.76-7.92 | vs |
| 16.281-15.784 | 5.44-5.61 | w |
| 19.959-19.451 | 4.445-4.56 | w-m |
| 23.053-22.433 | 3.855-3.96 | w-m |
| 28.401-27.681 | 3.14-3.22 | m-s |
| 32.778-32.054 | 2.73-2.79 | w-m |
| 34.673-34.129 | 2.585-2.625 | w-m |
| 36.696-36.086 | 2.447-2.487 | w-m |

or where said diffraction pattern has at least the d-spacings and intensities set forth in Table B when the material has the sitinakite topology:

TABLE B

| 2Θ | d(Å) | $I/I_0$% |
|---|---|---|
| 11.365-11.219 | 7.78-7.88 | vs |
| 18.071-17.374 | 4.905-5.100 | w |
| 22.696-22.628 | 3.915-3.926 | w |
| 26.88-26.253 | 3.314-3.392 | w-m |
| 27.627-27.065 | 3.226-3.292 | w-m |
| 32.357-32.163 | 2.765-2.781 | m-s |
| 34.68-34.049 | 2.585-2.631 | w-m |

or where said diffraction pattern has at least one peak with a d-spacing between 7 Å and 8 Å with a relative intensity of 100% when the material is a pharmacosiderite-sitinakite intergrowth or a mixture of pharmacosiderite, sitinakite and pharmacosiderite-sitinakite intergrowth phases in any combination.

2. The process of claim 1 wherein said small molecule heavy metal chelator is selected from 2,3-dimercaptopropanol, 2,3-dimercaptosuccinic acid, ethylenediaminetetraacetic acid, glutathione, and cysteine.

3. The process of claim 1 wherein the bodily fluid is selected from the group consisting of whole blood, blood plasma, or other component of blood, gastrointestinal fluids and dialysate solution containing blood, blood plasma, other component of blood or gastrointestinal fluids.

4. The process of claim 1 wherein the ion exchanger is packed into hollow fibers incorporated into a membrane.

5. The process of claim 1 wherein said ion exchanger is contained on particles coated with a coating comprising a cellulose derivative composition.

6. The process of claim 1 wherein said process is a hemoperfusion process wherein said bodily fluid is passed through a column containing said ion exchanger.

7. The process of claim 1 wherein a dialysate solution is introduced into a peritoneal cavity and then is flowed through at least one adsorbent bed containing at least one of said ion exchanger.

8. The process of claim 1 wherein said ion exchanger is formed into a shaped article to be ingested orally, followed by ion exchange between said ion exchanger and said $Pb^{2+}$ and, $Hg^{2+}$ toxins contained in a gastrointestinal fluid in a mammal's intestines and then by excretion of said ion exchanger containing said toxins.

9. The process of claim 8 wherein said shaped article is coated with a coating that is not dissolved by conditions within a stomach.

* * * * *